(12) United States Patent
Holopainen (10) Patent No.: US 11,828,387 B2
(45) Date of Patent: Nov. 28, 2023

(54) VALVES AND METHODS OF MAKING VALVES FOR RESTRICTING AIRFLOW TO AND/OR FROM A PATIENT

(71) Applicant: GE Precision Healthcare LLC, Wauwatosa, WI (US)

(72) Inventor: Timo Holopainen, Helsinki (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 85 days.

(21) Appl. No.: 17/565,610

(22) Filed: Dec. 30, 2021

(65) Prior Publication Data

US 2023/0213103 A1      Jul. 6, 2023

(51) Int. Cl.
*F16K 7/06*    (2006.01)
*A61M 16/20*    (2006.01)

(52) U.S. Cl.
CPC .............. *F16K 7/06* (2013.01); *A61M 16/201* (2014.02)

(58) Field of Classification Search
CPC . F16K 7/06; F16K 7/04; A60M 39/18; A60M 39/28
USPC .............................................. 251/7
See application file for complete search history.

(56) References Cited

U.S. PATENT DOCUMENTS

| | | | | |
|---|---|---|---|---|
| 143,907 A * | 10/1873 | Hyde | ............... | F16K 7/06 138/119 |
| 1,309,321 A * | 7/1919 | Fairweather | ............ | F41B 11/72 251/74 |
| 2,092,400 A * | 9/1937 | Miller | ................ | A61M 39/287 251/7 |
| 2,092,401 A * | 9/1937 | Miller | ................ | A61M 39/286 251/7 |
| 2,809,651 A * | 10/1957 | Moberg | .................... | F16K 7/06 292/307 R |
| 3,197,173 A * | 7/1965 | Taubenheim | ............. | F16K 7/06 24/527 |
| 3,874,042 A * | 4/1975 | Eddleman | ................ | F16K 7/04 251/10 |

(Continued)

FOREIGN PATENT DOCUMENTS

EP    3616740 A1    3/2020

OTHER PUBLICATIONS

E. Turbil et al., Does Endo-Tracheal Tube Clamping Prevent Air Leaks and Maintain Positive End-Expiratory Pressure During the Switching of a Ventilator in a Patient in an Intensive Care Unit? A Bench Study, Published Mar. 11, 2020, pp. 1-10.

(Continued)

*Primary Examiner* — Umashankar Venkatesan
(74) *Attorney, Agent, or Firm* — ANDRUS INTELLECTUAL PROPERTY LAW, LLP (57) ABSTRACT

A manually operable valve for restricting airflow to and/or from a patient. The valve includes a body having one or more walls that extend between a first end and a second end. The one or more walls form a passage between the first end and the second end of the body. Two moveable members are positioned on opposing sides of the passage and axially fixed between the first end and the second end of the body. The two moveable members are configured such that depressing the two moveable members inwardly deforms the one or more walls to thereby restrict the passage. When the two moveable members are subsequently released, the one or more walls return to unrestrict the passage.

19 Claims, 7 Drawing Sheets

(56) References Cited

U.S. PATENT DOCUMENTS

| | | | | | |
|---|---|---|---|---|---|
| 4,243,034 | A | * | 1/1981 | Brandt | A61M 39/286 251/6 |
| 4,382,453 | A | * | 5/1983 | Bujan | A61M 39/28 138/40 |
| 4,493,710 | A | * | 1/1985 | King | A61M 5/1689 128/DIG. 13 |
| 4,518,145 | A | * | 5/1985 | Keltz | F16K 7/06 251/8 |
| 5,088,522 | A | * | 2/1992 | Rath | F04B 43/0072 138/119 |
| 5,338,313 | A | * | 8/1994 | Mollenauer | A61M 39/0613 604/536 |
| 5,489,274 | A | * | 2/1996 | Chu | A61M 39/0613 604/248 |
| 11,384,849 | B2 | * | 7/2022 | Regen | F16K 7/06 |

OTHER PUBLICATIONS

T. McConick, Clamp to Prevent Collapse, Journal of the Association of Anaesthetists of Great Britain and Ireland, Published Jul. 5, 2010, pp. 857-866.

\* cited by examiner

VALVES AND METHODS OF MAKING VALVES FOR RESTRICTING AIRFLOW TO AND/OR FROM A PATIENT

FIELD

The present disclosure generally relates to valves and methods of making valves for restricting airflow to and/or from a patient.

BACKGROUND

One of the most important needs in respiratory care is the continuous maintenance of uninterrupted positive airway pressure for the patient. Modern ventilators, as well as anesthesia devices that also function as ventilators, are configured to provide positive airway pressure throughout the entire process of providing ventilation for a patient. One example of a ventilator available in the market is the Engstrom ventilator produced by GE Healthcare®.

However, this positive airway pressure must also be maintained when the patient is not connected to the ventilator. For example, the patient may be disconnected from the ventilator to clean various components within the breathing circuit or ventilator, to replace tubing and/or connectors, to change medical devices (e.g., from a ventilator to an anesthesia device), or to reposition or relocate the patient. Therefore, to maintain this positive airway pressure when the patient is no longer connected to the ventilator, a portion of the breathing circuit still connected to the patient may be temporarily occluded to prevent airflow therethrough. This is often done by pinching the breathing circuit closed at the intubation tube, an elbow, or a pre-measurement cuvette.

An occlusion device may be used to pinch the breathing circuit closed (or in other words, to create the occlusion), for example a clamp such as young scissors. For example, the clamp may be positioned between the corner piece and the cuvette to occlude the breathing circuit and thus prevent airflow to and/or from the patient. In other examples, the caregiver may uses their hands to occlude the breathing circuit. For example, the caregiver may fold the intubation tube or another portion of the breathing circuit, in some cases with multiple folds, to cause the occlusion.

Once the breathing circuit is occluded, other portions of the breathing circuit between the occlusion device and the ventilator may be disconnected without losing the positive airway pressure for the patient.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One example of the present disclosure generally relates to a manually operable valve for restricting airflow to and/or from a patient. The valve includes a body having one or more walls that extend between a first end and a second end. The one or more walls form a passage between the first end and the second end of the body. Two moveable members are positioned on opposing sides of the passage and axially fixed between the first end and the second end of the body. The two moveable members are configured such that depressing the two moveable members inwardly deforms the one or more walls to thereby restrict the passage. When the two moveable members are subsequently released, the one or more walls return to unrestrict the passage.

In certain examples, the body and the two moveable members are formed together of an elastomeric material.

In certain examples, the elastomeric material comprises silicone rubber.

Certain examples further include one or more fingers positioned between the two moveable members and the one or more walls. The one or more fingers are positioned to deform the one or more walls more than the two moveable members deform the one or more walls when the two moveable members are depressed inwardly. In certain examples, a first finger within the one or more fingers is positioned between a first of the two moveable members and the one or more walls, wherein a second finger within the one or more fingers is positioned between a second of the two moveable members and the one or more walls, and wherein the first finger is axially closer than the second finger to the first end of the body. In certain examples, a third finger within the one or more fingers is positioned between the first of the two moveable members and the one or more walls, where the second finger is axially positioned between the first finger and the third finger. In certain examples, the first finger and the third finger are fixed relative to the first of the two moveable members and the second finger is fixed relative to the second of the two moveable members.

In certain examples, the two moveable members each extend between a first end and a second end. Each of the two moveable members is coupled to the body at least at one of the first end and the second end corresponding thereto. In certain examples, at least one of the two moveable members both the first end and the second end thereof is coupled to the body, where the at least one of the two moveable members has a thickness, and where the thickness is reduced at the first end and at the second end relative to the thickness a midpoint therebetween. In certain examples, a center axis is defined through the passage extending between the first end and the second end of the body, where moveable member axes are defined between the first end and the second end of each of the two moveable members, respectively, and where the center axis and the moveable member axes remain in a same plane when the passage is restricted and when the passage is unrestricted.

In certain examples, the body has a first connection at the first end, a second connection at the second end, and a central portion therebetween, and the passage is cylindrically shaped through at least the central portion.

In certain examples, the body has a first connection at the first end, a second connection at the second end, and a central portion therebetween, and the valve further includes a flange that extends outwardly from the one or more walls at the first end of the body so as to prevent positioning the first connection within another connector.

In certain examples, the body has a first connection at the first end, a second connection at the second end, and a central portion therebetween. The first connection is configured to receive a first conduit within the passageway and the second connection is configured to receive a second conduit within the passageway such that valve fluidly couples the first conduit to the second conduit.

In certain examples, the body has a first connection at the first end, a second connection at the second end, and a central portion therebetween. A shelf extends outwardly from the body between the first connection and the central portion.

In certain examples, the two moveable members each extend between a first end and a second end, and the two moveable members have a rectangular cross section between the first end and the second end.

In certain examples, the passage is cylindrically shaped at the first end and at the second end, and the passage has a first inner diameter at the first end that is different than a second inner diameter at the second end. In certain examples, the passage has a third inner diameter at a point between the first end and the second end that is less than the first inner diameter and less than the second inner diameter.

The present disclosure further generally relates to a method for making a manually operable valve for restricting airflow to and/or from a patient. The method includes forming a body having one or more walls that extend between a first end and a second end. The one or more walls define a passage through the body between the first end and the second end. The method includes positioning two moveable members on opposing sides of the passage. The method further includes axially fixing the two moveable members between the first end and the second end of the body such that the two moveable members are configured to be depressed inwardly towards the passage. Depressing the two moveable members inwardly deforms the one or more walls to thereby restrict the passage. When the two moveable members are subsequently released, the one or more walls returns to unrestrict the passage.

In certain examples, the two moveable members are formed together of an elastomeric material, and the method further includes positioning a first finger between a first of the two moveable members and the one or more walls, and positioning a second finger between a second of the two moveable members and the one or more walls, where the first finger is axially closer than the second finger to the first end of the body.

The present disclosure further generally relates to a manually operable valve for temporarily restricting airflow to and/or from a patient. The valve includes a body having a wall that extend between a first end and a second end. The body has a first connection at the first end, a second connection at the second end, and a central portion therebetween. The wall forms a passage between the first end and the second end of the body. The first connection is configured to receive a first conduit within the passageway and the second connection is configured to receive a second conduit within the passageway such that valve fluidly couples the first conduit to the second conduit. The valve further includes first and second moveable members each having a first and second ends. The first and second moveable members are positioned on opposing sides of the passage and coupled at the first end and second ends to the body such that the first and second moveable members are axially fixed between the first end and the second end of the body. The first and second moveable members each have a thickness, and the thickness is reduced at the first and second ends relative to the thickness a midpoint therebetween. The valve further includes first and second fingers that extend towards the body from the first and second moveable members, respectively, where the first finger is axially closer than the second finger to the first end of the body. The first and second moveable members are configured such that depressing the first and second moveable members inwardly towards each other causes the first and second fingers to deform the wall to thereby restrict the passage, and when the first and second moveable members are subsequently released the wall returns to unrestrict the passage.

Various other features, objects and advantages of the disclosure will be made apparent from the following description taken together with the drawings.

BRIEF DESCRIPTION OF THE DRAWINGS

The present disclosure is described with reference to the following drawings.

DETAILED DISCLOSURE

The present inventor has recognized problems with the methods and devices presently known in the art for occluding breathing circuits. For example, the present inventor has recognized that the deformation caused by using clamps or folding over existing breathing circuits known in the art can cause damage to the breathing circuit. For example, these devices and methods can cause cracking or leaks from the breathing circuit, which results in inaccurate ventilation (in flow and/or pressure) for the patient. In the context of an anesthesia device, this can also cause anesthetic agent to leak from the breathing circuit. This results in an insufficient quantity of agent being delivered to the patient, and also accidental exposure of the agent to others in the room.

In circumstances in which leaks are not caused, the deformation can also impact the resistance of flow through the breathing circuit. For example, additional kinks in the breathing circuit caused by damage from occlusion can make the patient's airway pressure appear to the ventilator to be artificially elevated, resulting in insufficient pressure in the actual airway of the patient.

The present inventor has identified a further risk when clamps are used for creating the occlusion. Specifically, there is a possibility of the caregiver at least temporarily forgetting to remove the clamp after the patient is reconnected to the ventilator. This prolongs the amount of time that the patient goes without ventilation, and is thus detrimental to the patient's health.

Figure 1:
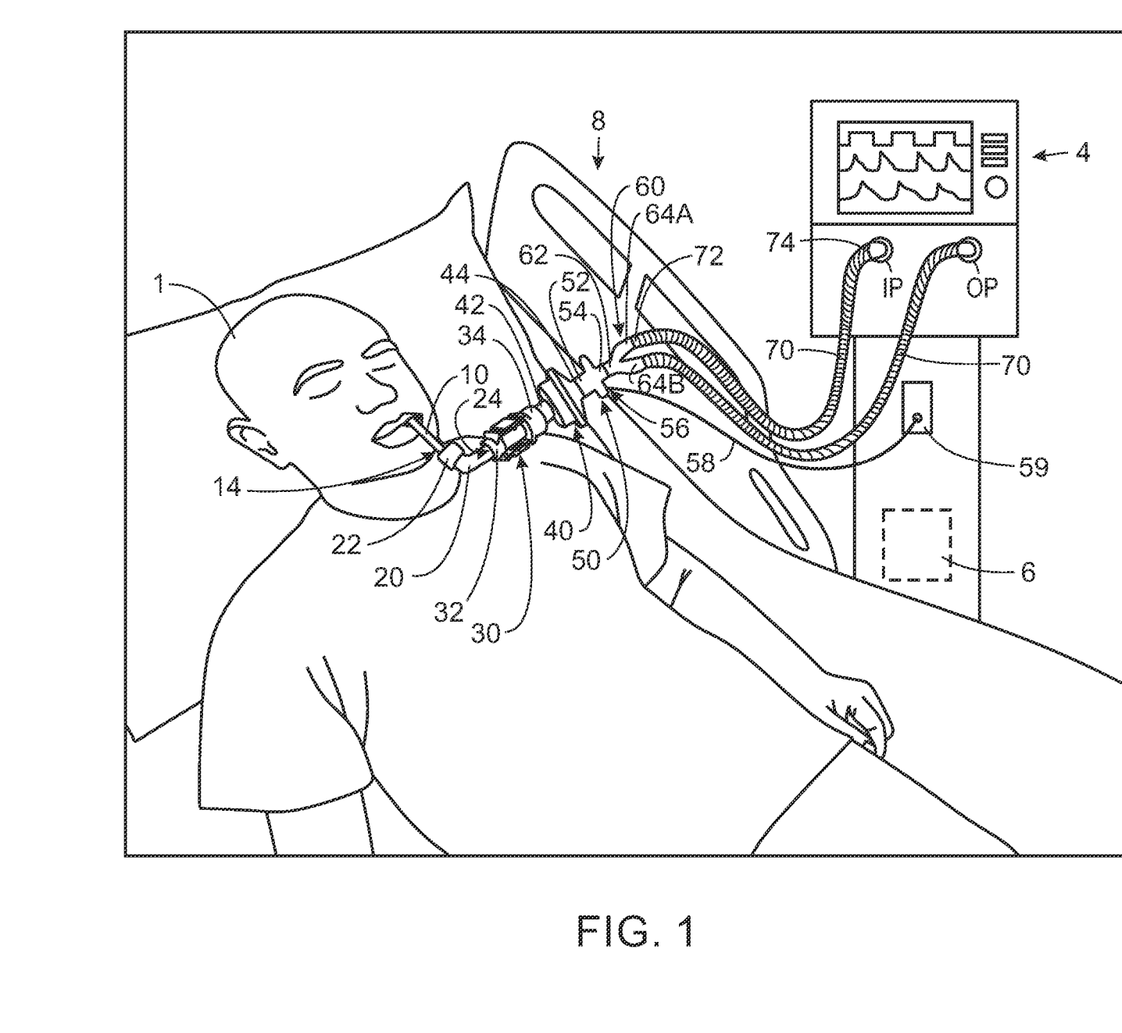
FIG. 1 is a perspective view of a valve for restricting airflow to and/or from a patient according to the present disclosure, connected within a breathing circuit between a patient and a medical device.

FIG. 1 shows a valve 30 according to the present disclosure, which enables a caregiver to temporarily occlude a breathing circuit 8 between a patient 1 and a medical device 4, such as a ventilator. Other than the valve 30 disclosed herein, the breathing circuit 8 may be comprised of conventional components. By way of example, each of the connections between adjacent components may be connected air-tight by press-fit arrangements. In particular, one end of one component may have a circular cross section with an outer diameter corresponding to an inner diameter at an end of another component received therein.

An intubation tube 10 has been positioned within the airway of the patient 1 in a conventional manner, extending out of the patient's mouth at a second end 14. The second end 14 of the intubation tube 10 is connected to an angle connector 20 in a conventional manner. In the example shown, the second end 14 of the intubation tube 10 is received within a first end 22 of the angle connector 20, whereby the angle connector 20 includes a 90 degree bend and extends to a second end 24.

The second end 24 of the angle connector 20 is connected to the valve 30, which extends between a first end 32 and a second end 34. In the example shown, the first end 32 of the valve 30 is configured to receive the second end 24 of the angle connector 20 therein. The second end 34 of the valve 30 is connected to a gas sensor connector 50. The gas sensor connector 50 extends from a first end 52 (here, received within the inner diameter of the second end 34 of the valve 30) to a second end 54. A port 56 is also provided within the gas sensor connector 50, which is connected to a spirometry device 59 within the medical device 4 via a line 58 in a manner known in the art.

The second end 54 of the gas sensor connector 50 is connected to a Y-piece 60. The Y-piece has a first end 62 that in the present example receives the second end 54 of the gas sensor connector 50 therein. The Y-piece 60 bifurcates from the first end 62 to two second ends 64A, 64B, respectively. The second ends 64A, 64B are connected to an inlet port IP and an outlet port OP of the medical device 4, respectively, via hoses 70 that each extend between a first end 72 and a second end 74. In certain examples, one or more of the components referenced above may not be present (e.g., the angle connector 20 or gas sensor connector 50), additional components may be incorporated (e.g., other sensor connectors), and/or two or more components may be combined together (e.g., a Y-piece 60 integrated with the hoses 70).

In this manner, the patient 1 is fluidly connected to the medical device 4 to receive ventilation therefrom (via breathing hardware 6 therein in a conventional manner), but with a valve 30 according to the present disclosure being incorporated serially within the breathing circuit 8 between the patient 1 and the medical device 4.

Figure 2:
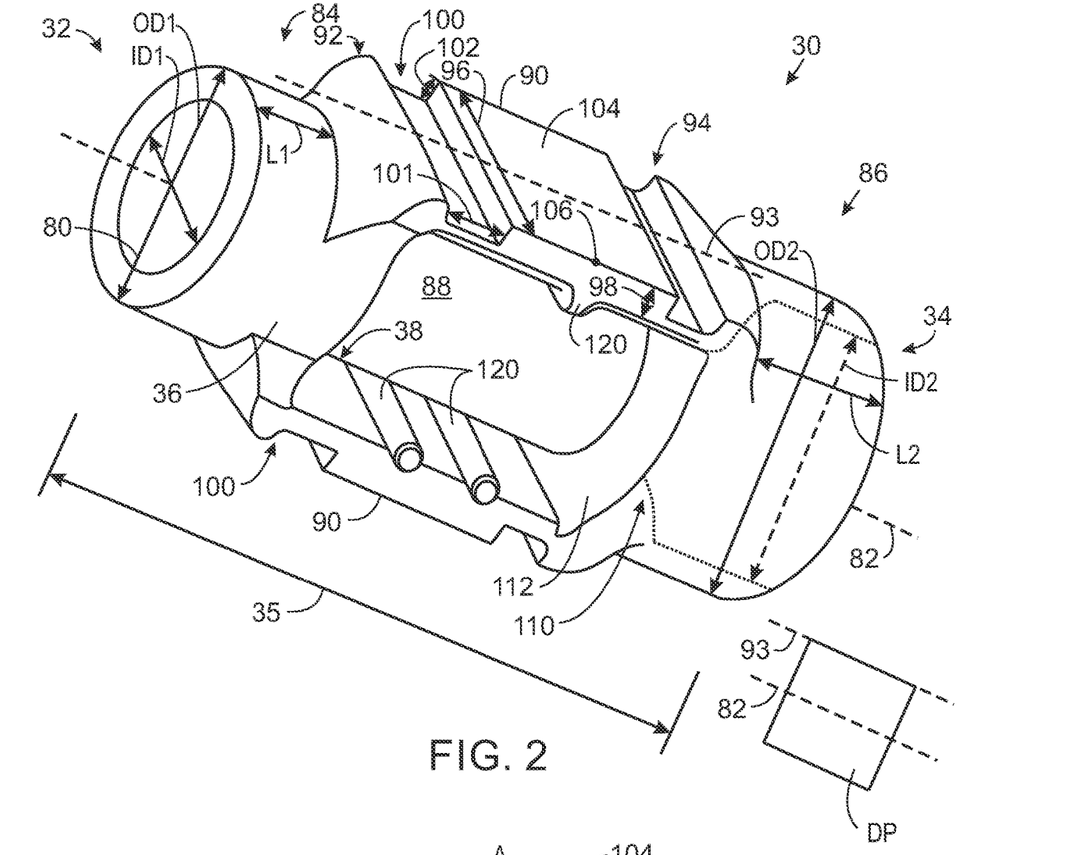
FIG. 2 is a close-up view of a valve such as shown in FIG. 1, shown in an open position.
Figure 3:
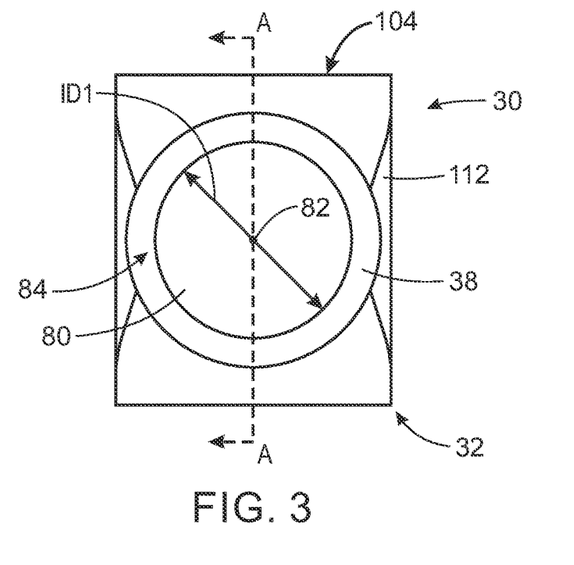
FIG. 3 is a front view of the valve shown in FIG. 2.
Figure 4:
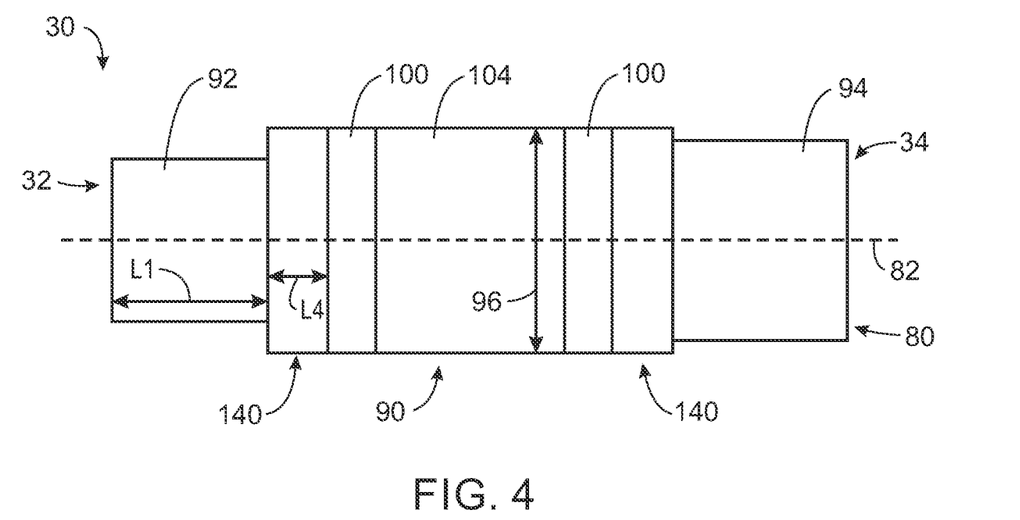
FIG. 4 is a top view of the valve shown in FIG. 2.

FIG. 2 is perspective view of a valve 30 according to the present disclosure. The valve 30 has a body 36 with one or more walls 38 that extend between the first end 32 and the second end 34 forming a length 35 therebetween. In the example shown in FIGS. 1 and 2, the walls 38 are a single, cylindrically shaped wall that forms a passage 80 extending within the interior thereof between the first end 32 and the second end 34. A central axis 82 is centrally defined through the passage 80 between the first end 32 and the second end 34.

A first connector 84 is provided at the first end 32 of the valve 30, which has an inner diameter ID1, an outer diameter OD1, and a length L1 defined parallel to the central axis 82 of the passage 80. A second connector 86 is provided at the second end 34 of the valve 30, which has an inner diameter ID1, an outer diameter OD2, and a length L2 defined parallel to the central axis 82 of the passage 80. The first connector 84 and the second connector 86 may be integrally formed with the body 36, or subsequently coupled to the body 36. Likewise, the first connector 84 and the second connector 86 may be comprised of the same or different materials compared to each other and/or to the body 36, as discussed further below.

With continued reference to FIG. 2, the inner diameters ID1 and ID2 at the first end 32 and the second end 34 are in certain examples 15 mm and 22 mm to mirror conventional components that may be coupled thereto. Additionally, the passage 80 may be cylindrically shaped the entire length between the first end 32 and the second end 34. However, it should be recognized that the inner diameters ID1, ID2, outer diameters OD1, OD2, and lengths L1, L2 may vary from each other and/or from what is shown. Likewise, the shape of the passage 80 may vary between the first end 32 and the second end 34. By way of example, the lengths L1 and L2 at the first end 32 and the second end 34 could each be between 5 mm and 20 mm, and/or the length 35 between the first end 32 and the second end 34 could be between 30 mm and 8 mm.

Figure 8:
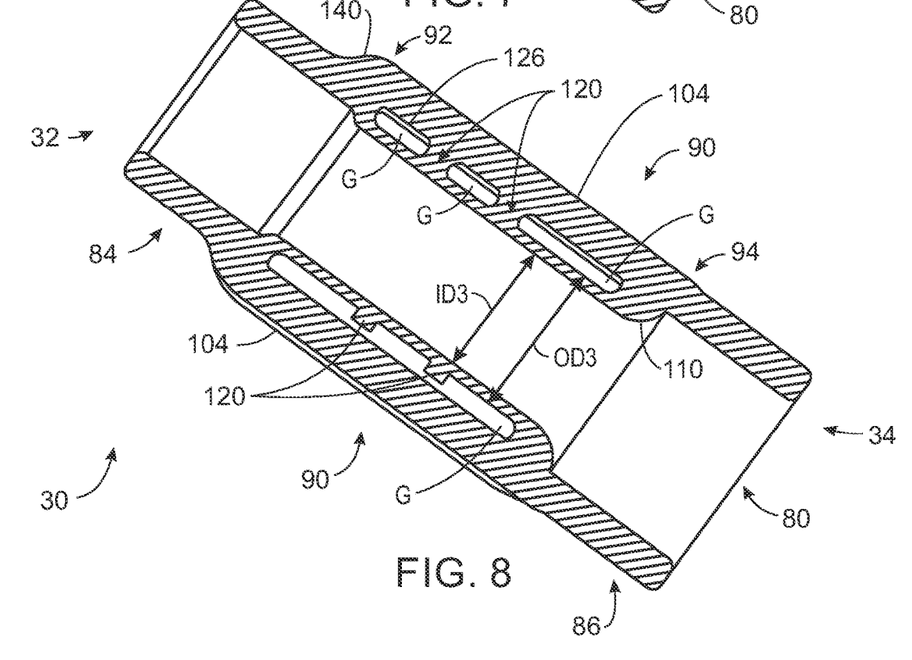
FIG. 8 is a sectional side view of another valve according to the present disclosure.

A central portion 88 of the valve 30 is provided between the first connector 84 and the second connector 86. In certain examples, the wall 38 is thinner (i.e., between the interior surface and the exterior surface) in the central portion 88 relative to the thickness of the wall 38 in least one of the first connector 84 and the second connector 86. In addition or in the alternative, an inner diameter ID3 (see FIG. 8) and/or outer diameter OD3 of the central portion 88 may be less than the corresponding inner diameters ID1, ID2 and/or outer diameters OD1, OD2 at the first connector 84 and the second connector 86. The difference in inner diameters ID1, ID2 may be accomplished by an inward tapering 110 of the inner diameters ID1, ID2 when progressing towards the central portion 88. Likewise, a difference in the outer diameters OD1, OD2 may be provided via a shelf 112 between the outer diameter ID3 of the central portion and the outer diameters OD1, OD2 of the first connector 84 and/or second connector 86. It should be recognized that the tapering 110 and shelves 112 discussed above may be incorporated elsewhere and/or used together to accomplish transitions in inner and outer diameters between the central portion 88 and the first connector 84 and/or second connector 86.

As shown in FIGS. 1 and 2, the first connector 84 and the second connector 86 are sized and shaped to be coupled to other components within the breathing circuit 8. In this example, the inner diameter ID1 of the first end 32 is configured to correspond the outer diameter of the second end 24 of the angle connector 20 and the inner diameter ID2 of the second end 34 is configured to correspond to the outer diameter of the first end 42 of the filter 40. In this manner, the passage 80 of the valve 30 forms an air-tight pathway between the angle connector 20 and the filter 40 in use.

Figure 9:
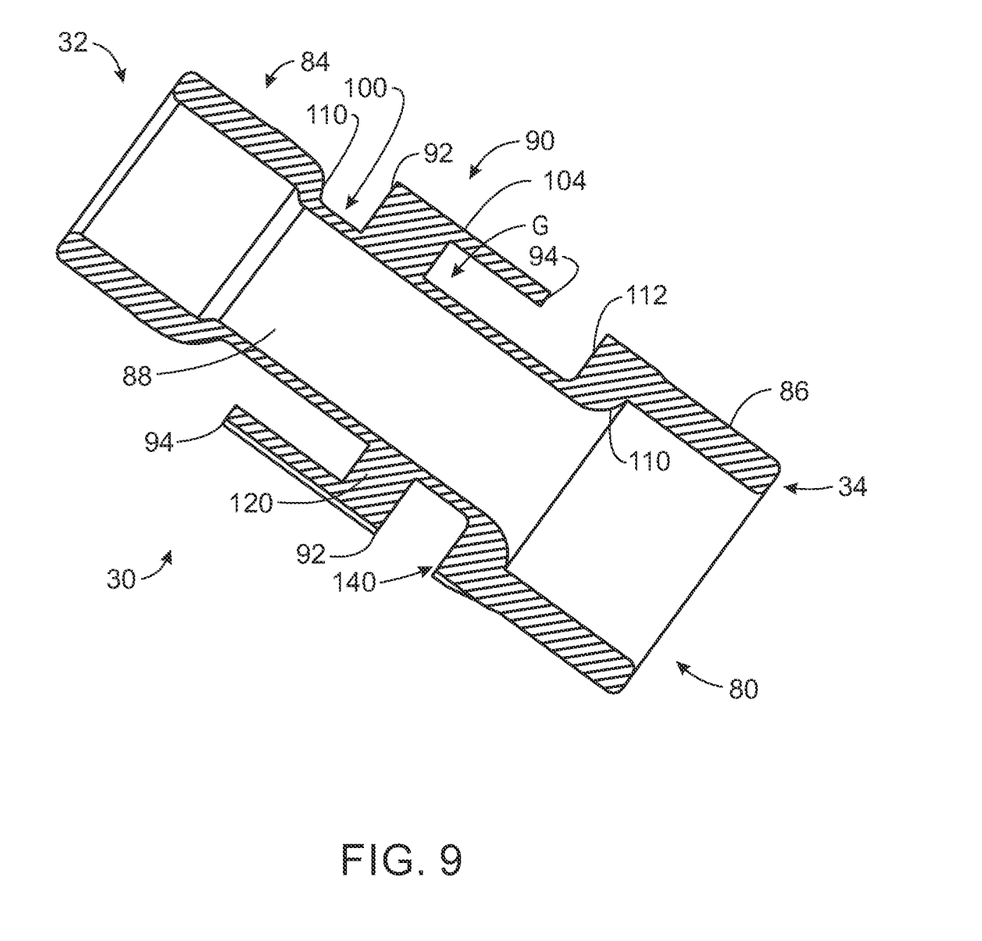
FIG. 9 is a sectional side view of another valve according to the present disclosure.

The valve 30 further includes two moveable members 90 positioned on opposite sides of the central portion 88 and the passage 80. The two moveable members 90 are each axially fixed between the first end 32 and the second end 34 of the body 36. Each of the two moveable members 90 extends between a first end 92 and a second end 94 defining a length therebetween along a moveable member axis 93 (see FIG. 2), as well as a width 96 and thickness 98. In certain embodiments, the moveable member axis 93 and the central axis 82 remain in the same depression plane DP throughout full operation of the valve 30, including a fully-open position (e.g., FIG. 5), a fully-closed position (e.g., FIG. 6), and additional positions therebetween. In the example of FIG. 2, the first ends 92 and the second ends 94 of the two moveable members 90 are each fixed to the body 36. However, in other examples, one or both of these sides may be free-floating, for example (e.g., FIG. 7 and FIG. 9).

As will be discussed further below, the two moveable members 90 are configured such that depressing the moveable members 90 inwardly deforms the one or more walls 38 to thereby restrict the passage 80. Furthermore, the moveable members 90 are also configured such that when subsequently released, the walls 38 return outwardly to the resting position shown in FIG. 2 to again unrestrict the passage 80. This ability to depress the moveable members 90 inwardly is provided by at least a portion of the moveable members 90 being resilient, and/or providing a resilient component or hinge between the body 36 and the moveable members 90. In certain examples, the moveable members 90 are made of a material including silicone rubber. In further examples, the entire valve 30 is formed of a single elastomeric material, for example silicone rubber. However, the present disclosure contemplates the use of differing materials for different components of the valve 30. As is discussed further below, the present inventor has developed the presently disclosed valve 30 such that depressing the moveable members 90 specifically causes the desired occlusion of the passage 80 without deforming the entire valve 30 in an uncontrolled manner.

For example, FIG. 2 shows one configuration in which the thickness 98 of two moveable members is reduced at one portion along the length thereof, here at both the first end 92 and the second end 94. In particular, thinner regions are created as channels 100 each having a depth 102 and a length 101 that extend the entire width 96 of each of the two moveable members 90. A contact surface 104 remains between the channels 100, here including a midpoint 106 between the first end 92 and the second end 94 of the moveable members 90. In this configuration, applying a force on the contact surfaces 104 inwardly (e.g., towards the passage 80, and towards each other) causes the moveable members 90 to deform to a greater extent due to the reduced thickness 98 at the channels 100. In other words, this increased deformation of the moveable members 90 between the channels 100 allows the contact surface 104 to move inwardly without deforming the first connector 84 and second connector 86 of the valve 30 (which would be detrimental to having airtight connections thereto).

Figure 5:
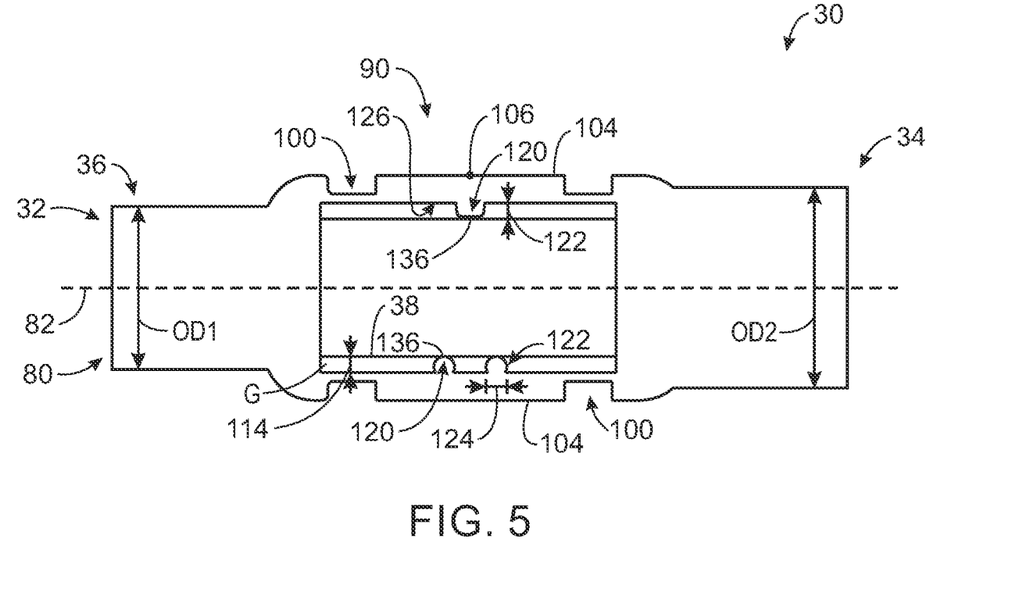
FIG. 5 is a side view of the valve shown in FIG. 2.
Figure 6:
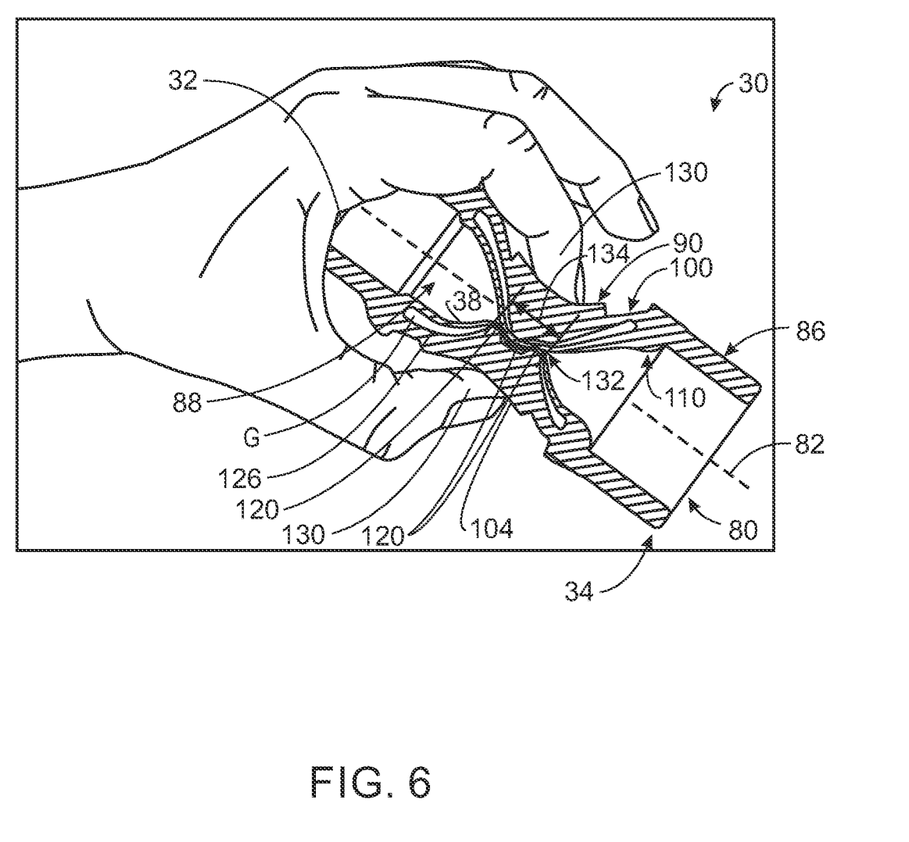
FIG. 6 is a sectional side view of a valve similar to that of FIG. 2 taken along the line A-A in FIG. 3, shown in a closed position.

As shown in FIG. 5, certain examples of valves 30 include a gap G having a height 114 between the moveable members 90 and the central portion 88. As will be discussed further below, at least some portions of the gap G are compressed down to a height 114 of zero when a force is applied to one or both of the contact surfaces 104, as shown in FIG. 6. The valve 30 shown in FIG. 5 also includes additional features provided between at least one of the moveable members 90 and the central portion 88, shown here as fingers 120.

In certain examples the widths of the fingers 120 are the same as the widths 96 of the moveable members 90 (see FIG. 2). As shown in FIG. 5, the fingers 120 also have heights 122 to a tip 136 and lengths 124 and may be shaped in different manners (e.g., having a rectangular prism cross-section along the width in certain examples, and a semi-circular prism cross-section in others, each shown in FIG. 5). The fingers 120 each extend transversely to the central axis 82 of the passage 80 through the body 36, but are parallel to the channels 100 defined in the moveable members 90. It should be recognized that the fingers 120 may extend at various angles relative to the central axis 82 while retaining the same function (e.g., at a 45 degree angle). The fingers 120 may be fixed to the exterior of the central portion 88 of the body 36 (e.g., FIG. 8), to the inward facing base 126 of the two moveable members 90 (e.g., FIG. 5), both (see FIG. 8), or neither (e.g., being separately positioned within the gap G, for example being fixed to another portion of the body 36).

The present disclosure contemplates different numbers and positions of fingers 120, including zero fingers 120. For example, the example of FIG. 5 has three fingers 120, whereas FIG. 8 has four fingers 120 and FIG. 9 has two fingers 120.

Returning to FIG. 5, it can be seen that the height 114 of the gap G is less (and in certain examples zero) between the fingers 120 and whichever of the exterior of the central portion 88 or the base 126 of the moveable members 90 opposes the fingers 120. The present inventor has recognized that varying the gap G across the length of the moveable members 90 in this manner provides that there is more deformation of the walls 38 of the central portion 88 with inward depression of the moveable members 90 where the fingers 120 are positioned. Moreover, the present inventor has recognized that by staggering the position of the fingers 120 along the central axis 82 (and in certain examples interdigitating the fingers 120 between the moveable members 90), an improved seal is formed between the interior surfaces of the walls 38 to restrict airflow through the passage 80 when the moveable members 90 are depressed inwardly towards each other.

FIG. 6 shows an example of a valve 30 similar to that of FIG. 5, now with a caregiver 130 applying a force on the contact surfaces 104 to depress the moveable members 90 inwardly towards each other. A finger 120 formed with an upper of the moveable members 90 is positioned axially between fingers 120 formed with a lower of the moveable members 90 such that the fingers 120 are interdigitated. This advantageously provides for a greater length 134 of the interior surface of the wall 38 through the central portion 88 being closed off by the fingers 120, thereby causing a strong occlusion 132 through the passage 80.

The present inventor has recognized that the heights 114 of the fingers 120 and the resilience of the walls 38 (e.g., via thickness and/or material) may be selected such that one or more of the fingers 120 deform the corresponding portions of the walls 38 past the central axis 82 of the passage 80 when fully depressed. In certain examples, the tip 136 (see FIG. 5) of a first finger 120 on a first moveable member 90 is closer that the tip 136 of a second finger 120 on a second moveable member 90 to the contact surface 104 of that second moveable member 90 when fully depressed, as shown in FIG. 6. This further zig-zag type positioning of the interior surface of the walls 98 improves the extent to which the occlusion 132 resists airflow through the passage 80.

The configuration of the channels 100, the height 114 of the gap G, and the properties of the material used for moveable members 90 and/or walls 38 in the central portion 88 may all be modified to impact the degree of deformation of the walls 38. Likewise, the relative sizing of the height 114 of the gap G, the heights 122 of the fingers 120, the thicknesses of the walls 38, and the inner diameter ID3 of the passage 80 through the central portion 88 may be modified to vary how much movement of the contact surface 104 is necessary to restrict the airflow to and/or from the patient through the passage 80.

The present inventor has further recognized that varying the materials used for the components of the valve 30 can further improve its ability to occlude the passage 80, and/or the effort required by the caregiver to do so. For example, the contact surface 104 and/or fingers 120 may comprise a more rigid material than other portions of the valve 30 (e.g., the central portion 88). By using more rigid materials, more of the force provided by the caregiver on the contact surfaces 104 is translated to deforming the central portion 88, rather than the contact surface 104 and/or fingers 120 absorbing some of the forces by deforming themselves.

Certain examples of valves 30 according to the present disclosure include additional features to improve the functionality and useability of the valve 30. For example, the valve 30 of FIG. 7 includes a projection 140 to assist with disconnecting the valve 30 from adjacent components within the breathing circuit. In particular, the projection 140 extends upwardly and outwardly by a height 142 from the wall 38 at the first end 32, the second end 34, and/or the central portion 88. The projection 140 is configured to be grasped by the caregiver, for example by the thumb, to remove the valve 30. Providing the projection 140 for grasping also reduces or eliminates pressure or pulling forces on more delicate portions of the valve 30 during removal, such as the moveable members 90 with the thinned channels 100. The projection 140 in certain examples also serves as an end-stop for other components that receive the valve 30 therein when connected (e.g., the first end 32 of the example of FIG. 8).

In other examples, the valve 30 includes features that prevent the valve 30 from being installed in an unintentional manner. For example, the valve 30 of FIG. 7 includes a flange 150 that prevents the first end 32 from being installed into another component, rather than receiving the other component within the inner diameters ID1, ID2 thereof. A flange 150 may also or alternatively be provided at the second end 34. The flange 150 extends as a disc having diameter 152 that is centered about the central axis 82 of the passage 80 and extends perpendicularly therefrom. A web 154 may be provided between the flange 150 and the wall 38 on the exterior of the first connector 84 portion of the valve 30 to provide support for the flange 150. The diameter 152 is designed to be larger than the inner diameters of other components within the breathing circuit, thereby preventing the first end 32 of the valve 30 from being inserted therein.

Figure 7:
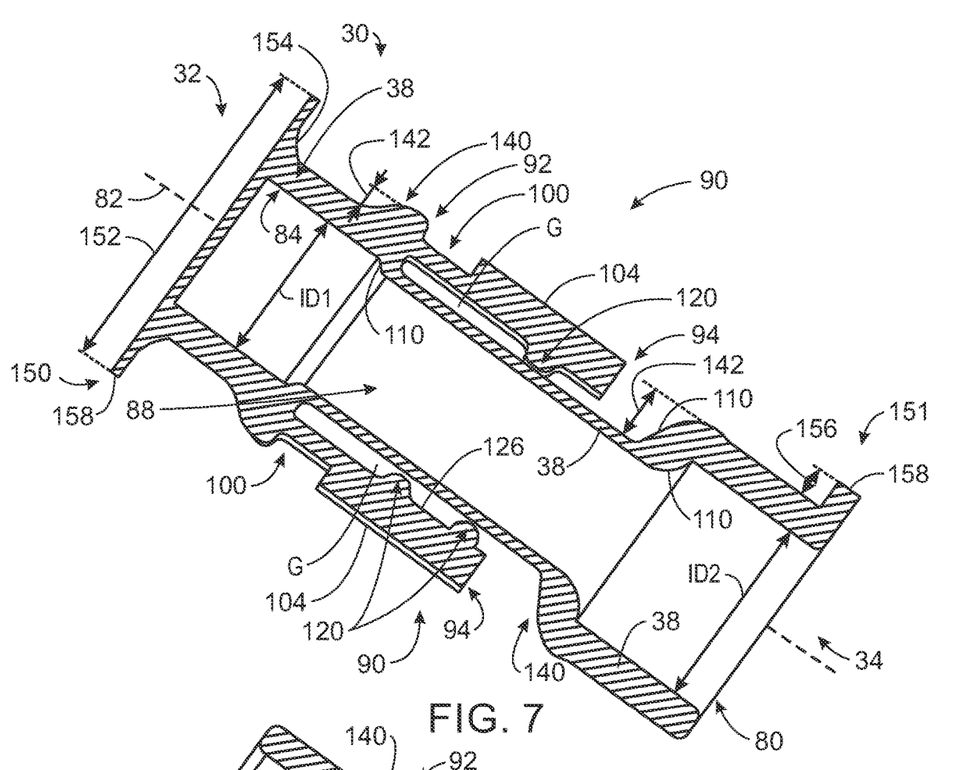
FIG. 7 is a sectional side view of another valve according to the present disclosure.

The valve 30 of FIG. 7 further includes a tab 151 at the second end 34. While providing a similar function as the flange 150, the tab 151 does not encircle the second end 34 as in the case of the flange 150 at the first end 32. Instead, the tab 151 extends away from the exterior surface of the wall 38 at the second end 34 by a height 156. The present inventor has recognized that in certain circumstances, the second end 34 can be prevented from being inserted within another component (when such a connection is unintended) with only minimal additional material. The width 158 of the flange 150 is selected to provide enough rigidity to prevent this incorrect installation, rather than merely folding down or distorting and allowing a caregiver to force the second end 34 within another component. Like the flange 150, tabs 151 may be provided at the first end 32 and/or the second end 34, including having a flange 150 at one end and a tab 151 at the opposite end, for example.

It should be recognized that in certain examples, the first end 32 and/or second end 34 of the valve 30 may be configured to be received within inner diameters of other components in the breathing circuit, in which case flanges 150 would not be used.

Figure 10:
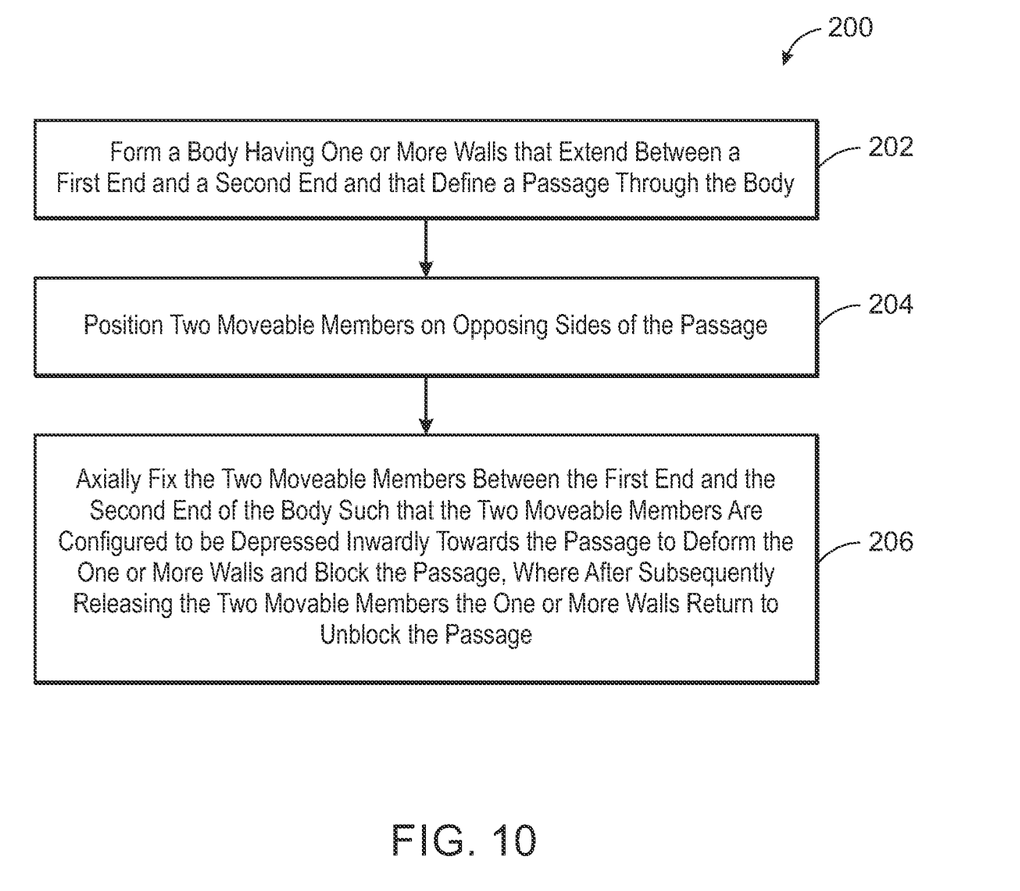
FIG. 10 is a process flow chart of a method for making a valve for restricting airflow to and/or from a patient according to the present disclosure.

FIG. 10 is a process flow of one example method 200 for making a making a manually operable valve for restricting airflow to and/or from a patient according to the present disclosure. Step 202 provides for forming a body having one or more walls that extend between a first end and a second end. The body is formed such that the one or more walls define a passage through the body between the first end and the second end. Step 204 provides for positioning two moveable members on opposing sides of the passage, which may be performed via integral formation of the two moveable members and the body, and/or through subsequent assembly.

Step 206 provides for axially fixing the two moveable members between the first end and the second end of the body such that the two moveable members are configured to be depressed inwardly towards the passage. Step 206 further provides that the valve is configured such that depressing the two moveable members inwardly deforms the one or more walls to thereby restrict the passage, and that when the two moveable members are subsequently released, the one or more walls returns to unrestrict the passage. As with step 204, step 206 may be performed via integral formation of the two moveable members and the body, and/or through subsequent assembly.

In this manner, a caregiver may temporarily, manually operate the valve 30 to restrict the airflow to and/or from the patient 1. As discussed above, this allows the caregiver to maintain positive airway pressure for the patient despite disconnecting portions of the breathing circuit 8, provided the disconnections are downstream of the patient relative to the valve 30. Since the valve 30 is manually operated, no additional clamps or tools are required to create the occlusion 132 (FIG. 6), therefore providing a streamlined and simplified process flow. Moreover, the use of the caregiver's own fingers also prevents damage to the valve 30, as there are no sharp edges and there is a limit to the shear force possible by the caregiver's own fingers.

The functional block diagrams, operational sequences, and flow diagrams provided in the Figures are representative of example architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A manually operable valve for restricting airflow to and/or from a patient, the valve comprising:
   a body having one or more walls that extend between a first end and a second end, wherein the one or more walls form a passage between the first end and the second end of the body; and two moveable members positioned on opposing sides of the passage and axially fixed between the first end and the second end of the body, wherein the body and the two moveable members are integrally formed of an elastomeric material, and wherein the two moveable members are configured such that depressing the two moveable members inwardly deforms the one or more walls to thereby restrict the passage, and when the two moveable members are subsequently released the one or more walls return to unrestrict the passage.

2. The valve according to claim 1, wherein the elastomeric material comprises silicone rubber.

3. The valve according to claim 1, further comprising one or more fingers positioned between the two moveable members and the one or more walls, wherein the one or more fingers are positioned to deform the one or more walls more than the two moveable members deform the one or more walls when the two moveable members are depressed inwardly.

4. The valve according to claim 3, wherein a first finger within the one or more fingers is positioned between a first of the two moveable members and the one or more walls, wherein a second finger within the one or more fingers is positioned between a second of the two moveable members and the one or more walls, and wherein the first finger is axially closer than the second finger to the first end of the body.

5. The valve according to claim 4, further comprising a third finger within the one or more fingers positioned between the first of the two moveable members and the one or more walls, wherein the second finger is axially positioned between the first finger and the third finger.

6. The valve according to claim 5, wherein the first finger and the third finger are fixed relative to the first of the two moveable members and the second finger is fixed relative to the second of the two moveable members.

7. The valve according to claim 1, wherein the two moveable members each extend between a first end and a second end, and wherein each of the two moveable members is coupled to the body at least at one of the first end and the second end corresponding thereto.

8. The valve according to claim 7, wherein for at least one of the two moveable members both the first end and the second end thereof is coupled to the body, wherein the at least one of the two moveable members has a thickness, and wherein the thickness is reduced at the first end and at the second end relative to the thickness a midpoint therebetween.

9. The valve according to claim 7, wherein a center axis is defined through the passage extending between the first end and the second end of the body, wherein moveable member axes are defined between the first end and the second end of each of the two moveable members, respectively, and wherein the center axis and the moveable member axes remain in a same plane when the passage is restricted and when the passage is unrestricted.

10. The valve according to claim 1, wherein the body comprises a first connection at the first end, a second connection at the second end, and a central portion therebetween, and wherein the passage is cylindrically shaped through at least the central portion.

11. The valve according to claim 1, wherein the body comprises a first connection at the first end, a second connection at the second end, and a central portion therebetween, further comprising a flange that extends outwardly from the one or more walls at the first end of the body so as to prevent positioning the first connection within another connector.

12. The valve according to claim 1, wherein the body comprises a first connection at the first end, a second connection at the second end, and a central portion therebetween, wherein the first connection is configured to receive a first conduit within the passageway and the second connection is configured to receive a second conduit within the passageway such that valve fluidly couples the first conduit to the second conduit.

13. The valve according to claim 1, wherein the body comprises a first connection at the first end, a second connection at the second end, and a central portion therebetween, and wherein a shelf extends outwardly from the body between the first connection and the central portion.

14. The valve according to claim 1, wherein the two moveable members each extend between a first end and a second end, and wherein the two moveable members have a rectangular cross section between the first end and the second end.

15. The valve according to claim 1, wherein the passage is cylindrically shaped at the first end and at the second end, and wherein the passage has a first inner diameter at the first end that is different than a second inner diameter at the second end.

16. The valve according to claim 15, wherein the passage has a third inner diameter at a point between the first end and the second end that is less than the first inner diameter and less than the second inner diameter.

17. A method for making a manually operable valve for restricting airflow to and/or from a patient, the method comprising:
    forming a body having one or more walls that extend between a first end and a second end, wherein the one or more walls define a passage through the body between the first end and the second end;
    forming two moveable members to be positioned on opposing sides of the passage and to be axially fixed between the first end and the second end of the body such that the two moveable members are configured to be depressed inwardly towards the passage, wherein depressing the two moveable members inwardly deforms the one or more walls to thereby restrict the passage, and wherein when the two moveable members are subsequently released the one or more walls returns to unrestrict the passage, wherein the body and the two moveable members are integrally formed of an elastomeric material.

18. The method according to claim 17, further comprising positioning a first finger between a first of the two moveable members and the one or more walls, and positioning a second finger between a second of the two moveable members and the one or more walls, wherein the first finger is axially closer than the second finger to the first end of the body.

19. A manually operable valve for temporarily restricting airflow to and/or from a patient, the valve comprising:
    a body having a wall that extend between a first end and a second end, wherein the body comprises a first connection at the first end, a second connection at the second end, and a central portion therebetween, wherein the wall forms a passage between the first end and the second end of the body, wherein the first connection is configured to receive a first conduit within the passageway and the second connection is configured to receive a second conduit within the passageway such that valve fluidly couples the first conduit to the second conduit;

first and second moveable members each having a first and second ends, the first and second moveable members being positioned on opposing sides of the passage and coupled at the first end and second ends to the body such that the first and second moveable members are axially fixed between the first end and the second end of the body, wherein the first and second moveable members each have a thickness, and wherein the thickness is reduced at the first and second ends relative to the thickness a midpoint therebetween; and first and second fingers that extend towards the body from the first and second moveable members, respectively, wherein the first finger is axially closer than the second finger to the first end of the body;

wherein the first and second moveable members are configured such that depressing the first and second moveable members inwardly towards each other causes the first and second fingers to deform the wall to thereby restrict the passage, and when the first and second moveable members are subsequently released the wall returns to unrestrict the passage.

* * * * *